(12) United States Patent
Martin

(10) Patent No.: US 11,564,377 B2
(45) Date of Patent: Jan. 31, 2023

(54) DURABLE PET DIAPER AND METHOD OF USING THE SAME

(71) Applicant: Microfine, Inc., Winston-Salem, NC (US)

(72) Inventor: John Martin, Winston-Salem, NC (US)

(73) Assignee: MICROFINE, INC., Winston-Salem, NC (US)

( * ) Notice: Subject to any disclaimer, the term of this patent is extended or adjusted under 35 U.S.C. 154(b) by 739 days.

(21) Appl. No.: 15/909,921

(22) Filed: Mar. 1, 2018

(65) Prior Publication Data
US 2018/0249681 A1   Sep. 6, 2018

Related U.S. Application Data

(60) Provisional application No. 62/465,890, filed on Mar. 2, 2017.

(51) Int. Cl.
| | |
|---|---|
| *A61F 13/15* | (2006.01) |
| *A01K 23/00* | (2006.01) |
| *A61F 13/49* | (2006.01) |
| *A61F 13/511* | (2006.01) |

(52) U.S. Cl.
CPC ........ *A01K 23/00* (2013.01); *A61F 13/49004* (2013.01); *A61F 13/511* (2013.01); *A61F 2013/15186* (2013.01)

(58) Field of Classification Search
CPC .. A61F 13/49004; A61F 13/511; A61F 13/15; A61F 2013/15186; A01K 23/00
See application file for complete search history.

(56) References Cited

U.S. PATENT DOCUMENTS

| | | | | |
|---|---|---|---|---|
| 5,518,761 A | * | 5/1996 | Hatsuda | A61F 13/15 427/180 |
| 5,555,847 A | * | 9/1996 | Kelly | A01K 23/00 119/850 |
| 2003/0208176 A1 | * | 11/2003 | Waksmundzki | A61F 13/53743 604/378 |
| 2006/0282052 A1 | * | 12/2006 | Saito | C08J 3/20 604/372 |
| 2010/0120940 A1 | * | 5/2010 | Adachi | A61L 15/42 523/111 |
| 2013/0036989 A1 | * | 2/2013 | Pesale | A01K 23/00 119/850 |
| 2014/0107606 A1 | * | 4/2014 | Komatsubara | A61D 99/00 604/391 |
| 2015/0313186 A1 | * | 11/2015 | Komatsubara | A01K 23/00 119/869 |

* cited by examiner

*Primary Examiner* — Jacqueline F Stephens
(74) *Attorney, Agent, or Firm* — FisherBroyles, LLP

(57) ABSTRACT

Herein disclosed is a durable, ecofriendly, pet diaper fabricated from durable, washable materials enabling repeated use is disclosed. The diaper includes an impervious exterior layer and a pervious and breathable interior layer joined at an outer rim. An absorbent pad is positioned distally from the outer rim creating a gap between the pad and outer rim. The diaper includes securing members and is designed for maximum comfort and commodious fit to the animal.

17 Claims, 7 Drawing Sheets

DURABLE PET DIAPER AND METHOD OF USING THE SAME

CROSS REFERENCE OF RELATED APPLICATIONS

This application claims the benefits of U.S. provisional application No. 62/465,890, filed Mar. 2, 2017 and entitled DURABLE PET DIAPER AND METHOD OF USING THE SAME, which provisional application is incorporated by reference herein in its entirety.

FIELD

A durable pet diaper and method for using the same is provided. The durable pet diaper is fabricated from durable, washable, and reusable materials that are easy to maintain and assembled to create a commodious fit on the pet's body.

BACKGROUND

It is known that a diaper is a type of underwear that allows the wearer to defecate or urinate without the use of a toilet by absorbing or containing waste products to prevent soiling of outer clothing or the external environment. When diapers become soiled, they require changing. Often, an animal, including household pets, are incontinent and therefore require use of a pet diaper. For example, whether as a result of advanced age, medical condition, or natural physiological processes, dogs and cats may exhibit a permanent or temporary inability to control their waste discharges, particularly urinary discharges, leading to numerous and problematic waste discharge in the home, automobile, etc. Moreover, female dogs and cats in estrus may secrete blood or other estrus related fluids which a pet owner may desire to contain. Pet owners visiting ether residences (e.g., friends and family) as well as owners traveling long distances may not, be in a position to walk their pets and pet waste containment is desirable.

Generally, such pet diapers are based on disposable pamper-style diapers for humans, but are adapted for use of four-legged animals having tails. The diaper for a pet has a structure that increases the length of the inguinal area of the pet, and contains a tail hole to enable passage of the tail. However, most diapers are not intended for reuse, creating an expensive proposition of replacement after every waste discharge. Diapers that are designed for reuse often contain a disposable and replaceable insert that is not ecofriendly or odor controlling. Also, these pet diapers often do not fit the pet comfortably, unnecessarily expose skin surface to wet material causes abrasion and irritation, and/or do not provide the needed protection for the pets. In addition, these pet diapers frequently slide off male pets and do not properly accommodate the anatomical differences between male and female pets often resulting in exposure of a male pet's penis to the outside environment. Moreover, male pet urine has a tendency to spray (squirt) out of the diaper due to location of the male urethra.

Other proposals have involved pet diapers. The problem with these diapers is that they are not reusable or washable. Also, the pet diapers do not fit the pet comfortably and securely, so as to enable optimal free movement by the pet while remaining secured. Even though the above cited pet diapers meet some of the needs of the market, a durable washable pet diaper configured for incontinent pets, fabricated from materials that enable reusability and washing, and tailored to fit commodiously on the pet's body for optimal pet comfort, is still desired.

SUMMARY

Provided herein is a durable pet diaper and method for using the same. The unrestrictive pet diaper can be configured for incontinent pets, providing a durable, reusable, washable diaper that fits commodiously on the pet's body. The durable, reusable pet diaper provides an impervious exterior layer and a breathable, pervious interior layer that encapsulate an absorbent pad that, in some embodiments, is multi-plied. The absorbent pad can be configured to fold multiple times, so as to form a small space profile between inner and outer layers. The folding increases the thickness and rigidity of the pad which, along with other factors, generates a pocketing or cupping effect that helps to reduce contact between a wet pad and the animal's skin thereby reducing abrasion and irritation. The pocketing or cupping effect, furthermore, increases the roominess of the design enhancing comfort to the animal. The absorbent pad does not have to be folded, however, to produce the cupping effect as other techniques may be employed to increase stiffness and/or thickness. The absorbent pad can also be positioned distally from an outer rim of the diaper to create a gap, such that the pet has additional space to move and scratch with the hind legs.

The unrestrictive pet diaper further provides one or more resilient flaps that extend from a front portion of the diaper. The flaps comprise one or more first securing elements that fasten to at least one second securing element disposed on a back portion of the diaper. The flaps are sufficiently resilient to extend and retract longitudinally across the pet's midsection so as to enable unrestricted movement and a commodious fit for the pet.

The unrestrictive pet diaper further provides foldable edges at the front portion of the diaper. The foldable edges are configured to be folded in, or extended outwardly, so as to enable the surface area of the pet's body that is covered by the front portion of the pet diaper to be increased or decreased. The unrestrictive pet diaper further provides an elasticized tail hole that provides unrestricted movement to the tail.

The outer fabric cover comprises a substantially impervious exterior layer which, in use, is the side that is not in contact with the pet's skin or fur. In one embodiment, the exterior layer comprises a laminate such as a polyvinyl chloride, which can be heat bonded or extruded onto a soft lightweight durable fabric. In one embodiment, the exterior layer comprises a low or non-wicking fabric to contain the moisture within the absorbent pad and prevent exterior wetness. The outer fabric cover further comprises a substantially pervious and breathable interior layer. The interior layer can be bound or affixed to the substantially impervious exterior layer along the outer edges or outline of the diaper. The interior layer and exterior layer may be sewn together with stitching confined along all or part of an outer rim of the diaper including, in some embodiments, around the elasticized tail hole. In one embodiment, the thread used for the stitching is low or non-wicking thread. This creates a durable and reusable material fabric configuration that allows for multiple washes from the same diaper.

In one embodiment, the absorbent pad can be folded into a first fold and a second fold along a pair of long sides. The bi-folded design elevates the portion of the absorbent pad off of the exterior layer, almost doubles its thickness across most of the absorbent pad, and decreases the width and profile of the absorbent pad, thereby forming the gap between the absorbent pad and the outer rim stitching and elastic. Additionally, the increased thickness and pad rigidity created by folding produces a cupping effect that helps to reduce contact between a wet pad and the animal's skin. In some embodiments, this effect may be accomplished using other techniques that increase the thickness and rigidity of the pad during manufacturing as an alternative to folding.

The absorbent pad can be multi-plied nonwoven fabric, each ply fabricated from a blend of polyolefin polymer (e.g., polypropylene or polyethylene) fibers, polyester fibers, and/or cotton/rayon fibers. In one embodiment, the fibers are blended through a process called mechanical entanglement using heat to set the bond of the polyolefin. Other nonwovens or woven/nonwoven hybrid fabrics can also be used and produced by processes such as stitchbonding, chemical bonding, thermal bonding or hydroentangling and the like. Nonwoven fabrics can be formed from processes well known in the art, for example, blending, melt blown, air laid, wet laid, carding, spun laid, flash spun and the like. Once the sheet or web is formed, the fabric can be bonded together by various methods including but not limited to thermal bonding, hydroentanglement ultrasonic patter bonding, needle pub chin or needle felting, chemical bonding and the like.

In one aspect, a durable washable pet diaper, comprises:

an outer fabric cover comprising a substantially impervious exterior layer and a substantially pervious and breathable interior layer, the layers being joined together along an outer rim of the diaper;

an absorbent pad being encapsulated between the exterior layer and the interior layer, the absorbent pad being folded into at least a first fold and a second fold along a pair of long sides of the absorbent pad, whereby the folds decrease the width and profile of the absorbent pad, forming a gap between the long sides of the absorbent pad and the outer rim of the diaper, whereby the folds increase the thickness of the absorbent pad;

a front portion substantially covering from the pet's crotch to the rib cage, the front portion comprising a foldable front edge adapted to fold outwardly and inwardly, whereby the front portion adjustably increases and decreases the surface area covered from the pet's crotch to the rib cage;

one or more resilient flaps extending from the front portion of the diaper, the flaps comprising one or more first securing elements; and a back portion substantially covering from the pet's rectum to the back, the back portion being defined by a tail hole, the back portion comprising at least one second securing element adapted to detachably mate with the first securing elements, whereby the flaps secure the front portion and the back portion of the diaper to the pet, whereby the flaps adjustably extend and retract longitudinally across, the pet's midsection when securing the front and back portions to the pet.

In another aspect, the impervious exterior layer comprises a laminate.

In another aspect, the laminate comprises polyvinyl chloride.

In another aspect, the impervious exterior layer comprises a soft lightweight durable fabric.

In another aspect, the soft lightweight durable fabric comprises a polyester mesh fabric.

In another aspect, the laminate is heat bonded to the soft lightweight durable fabric.

In another aspect, the one or more flaps comprises two elongated flaps having rounded edges.

In another aspect, the first securing elements and the second securing elements comprise hook and loop fasteners.

In another aspect, the exterior layer and the interior layer are joined at the outer rim through stitching or welding.

In another aspect, the exterior layer and the interior layer form a pocket.

In another aspect, the absorbent pad is disposed in the pocket.

In another aspect, the absorbent pad is stitched directly to the exterior and interior layers.

In another aspect, the absorbent pad is multi-plied.

In another aspect, the absorbent pad is fabricated from at least one of the following: a polyolefin polymer fiber, a polyester fiber, a cotton fiber, a rayon fiber, and a binder fiber.

In another aspect, the absorbent pad fibers are blended through mechanical entanglement to form webs or sheets which are bound together by thermal bonding thereby setting the bond of the polyolefin polymer fiber.

In another aspect, each ply of the absorbent pad has a different configuration of fibers.

In another aspect, the fibers include at least one of the following: an antimicrobial agent, a deodorant, and an antifungal agent.

In another aspect, the tail hole is elasticized.

One objective is to provide a durable and launderable pet diaper that can be used multiple times before discarding due to the material fabrication and durable construction.

Another objective is to provide a washable pet diaper.

Another objective is to provide a multi-plied absorbent pad that absorbs and retains a substantial amount of pet waste.

Another objective is to provide a diaper having a breathable interior layer for comfort of the pet.

Another objective is to provide an impervious outer layer to contain the moisture inside the diaper and inhibit escape to the exterior environment.

Another objective is to make the impervious outer layer soft.

Another objective is to create an unrestrictive commodious fit on the pet's rear body by decreasing the width and profile of the absorbent pad; and thereby forming a gap between the absorbent pad and the outer rim stitching and elastic.

Yet another objective is to provide fastenable flaps that can be adjusted across the length of the pet's midsection and ribcage to create a comfortable fit.

Yet another objective is to provide a tail hole that creates freedom of movement for the tail.

Yet another objective is to help incontinent pets discharge waste in a sanitary, efficient manner.

Yet another objective is to reduce costs of pet care by reusing the pet, diaper.

Yet another objective is to create environmental sustainability by reusing the pet diaper.

Yet another objective is to provide an inexpensive to manufacture pet diaper.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION

Figure 1:
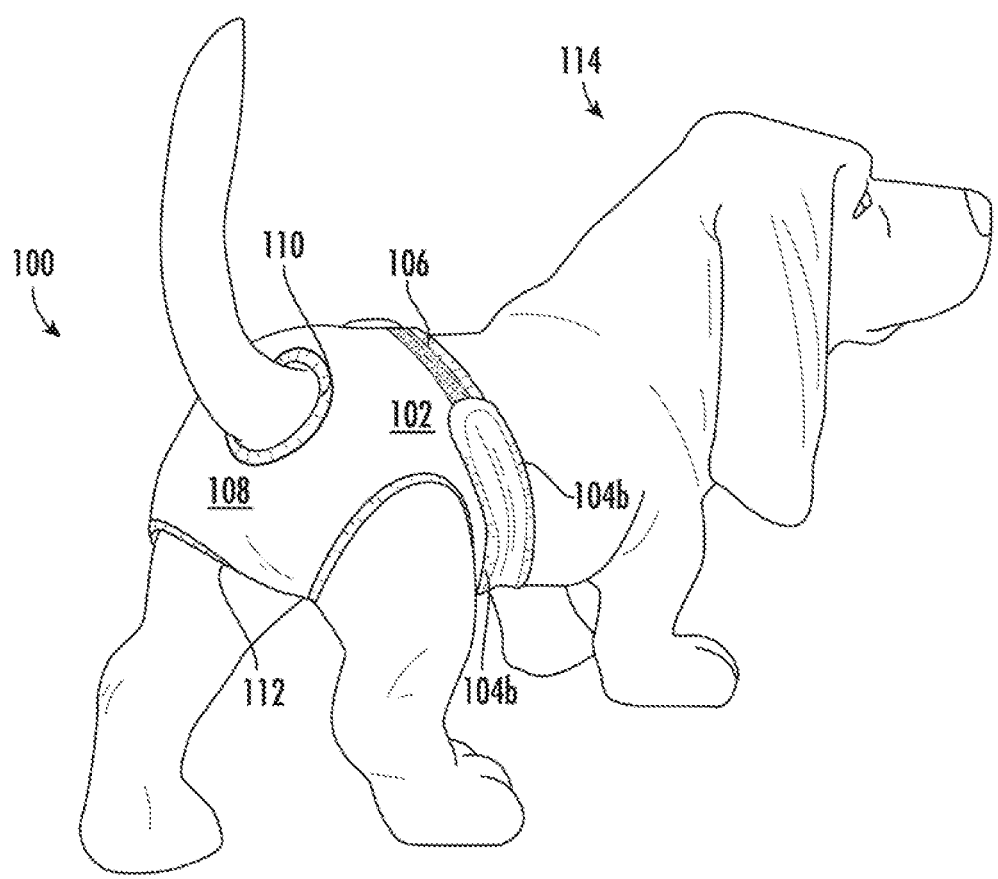
FIG. 1 illustrates a perspective view of an exemplary durable pet diaper being worn by a pet.

The following, detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "first," "second" "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

In one embodiment of the present invention, presented in FIGS. 1-7, a durable and washable pet diaper 100, and method 700 of diapering provides a unique pet diaper 100 adapted for reusability and comfort of incontinent pets. As referenced in FIG. 1, the durable washable pet diaper 100, hereafter "diaper 100" is fabricated from durable, washable materials that are easy to maintain and reuse, so as to reduce pet care costs and promote environmental sustainability. The material construction of the diaper 100 can also use odor preventive and germ-killing agents. The diaper 100 also has a unique tailored configuration that creates a commodious fit on the pet's body through use of a front foldable edge 106, an absorbent pad 204 defined by a narrow space profile, length adjustable and resilient fastening flaps 104a, 104b, and an elasticized tail hole 110. These features create a comfortable fit that helps incontinent pets discharge waste in a sanitary, efficient manner.

Attention is now directed to FIG. 1 of the drawings where the diaper 100 of the present disclosure is shown. The diaper 100 shown in FIGS. 5 and 6 has been cut in half for demonstration purposes and it should be understood that the diaper will be produced and sold as a single undivided unit. The view in FIGS. 1-4 shows the shape of the diaper 100 and includes features important to its successful use. As will be understood, the diaper 100 can be scaled to accommodate different sizes and shapes, as well as anatomical variation, in animal pets. It is believed that the description given hereinafter will suffice for a representative size, and it can be scaled from that size to other sizes. The pet on which the diaper is fitted may include, without limitation, a dog, a cat, a monkey, a gerbil, and various farm livestock.

Figure 2:
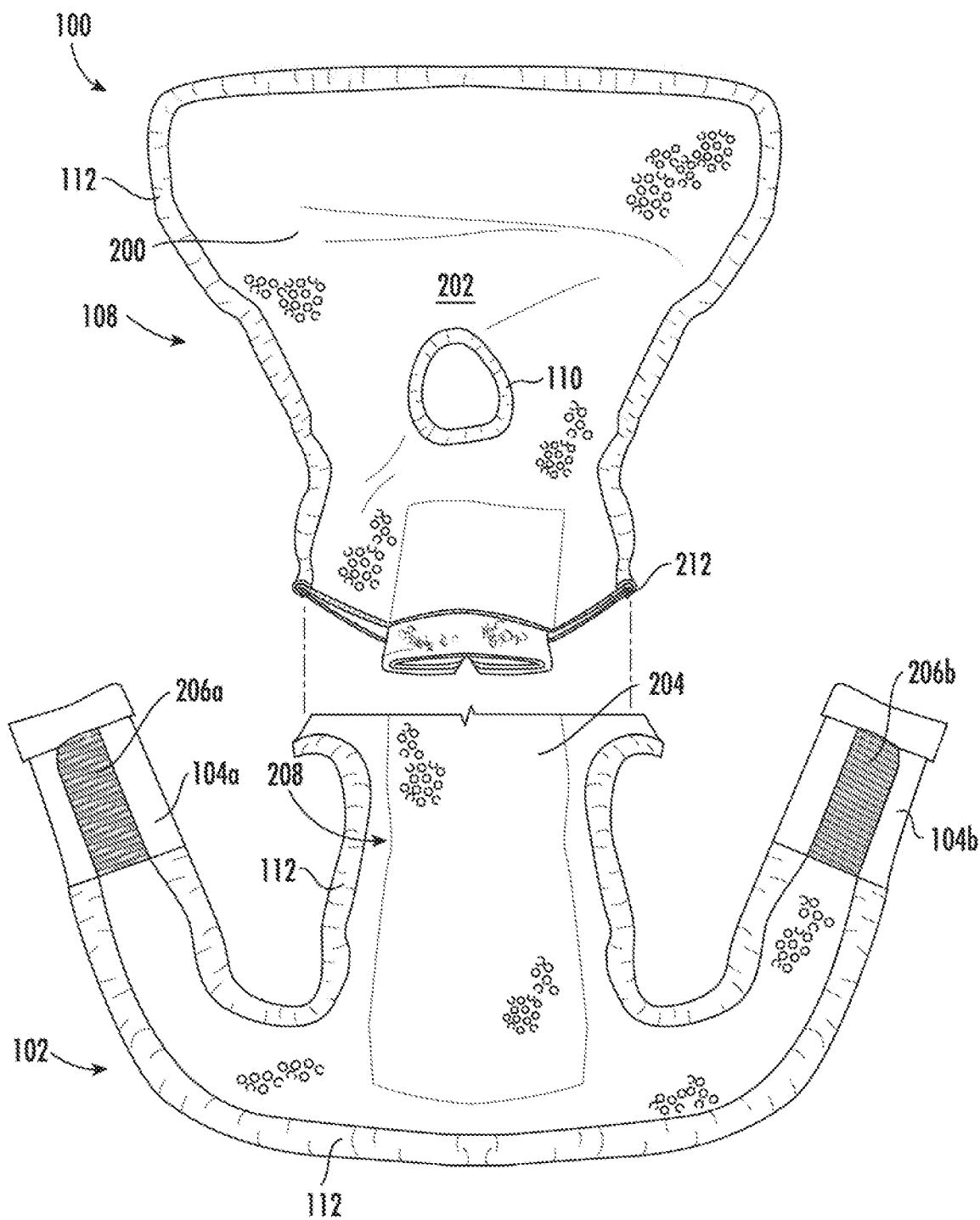
FIG. 2 illustrates a top view of the durable pet diaper showing the pervious and breathable layer, in accordance with an embodiment of the present invention.

Turning now to FIG. 2, the diaper 100 comprises an outer fabric cover 200 that is external to the pet's skin or fur, facing the environment, when fitted to the pet 114. The outer fabric cover 200 comprises a substantially impervious exterior layer 300 and a substantially pervious and breathable interior layer 202. The layers 202, 300 are joined together along an outer rim 112 of the diaper 100. In one non-limiting embodiment, the layers 202, 300 are joined at the outer rim 112 through stitching or welding. Though other means of fusing the layers 202, 300 may also be used, including: an adhesive, a snap button, a pin, a tying string, and the like. When joined at the outer rim 112 in such a manner, the exterior layer 300 and the interior layer 202 form a pocket 400. As discussed below, the pocket 400 is sized and dimensioned to securely contain a multi-plied absorbent pad 204 having a discrete space profile.

In one embodiment, the impervious properties of the exterior layer 300 help to prevent urine or other waste from seeping through to the outside environment. In one non-limiting embodiment, the exterior layer 300 comprises a rigid, or semi-rigid laminate 402. The laminate 402 is configured across the surface of the exterior layer 300 to create rigidity and structural integrity to the diaper 100. In one non-limiting embodiment, the laminate 402 comprises polyvinyl chloride, though in other embodiments, other well-known and available materials may be used as an impervious barrier film which can be bonded to the durable fabric 302 (described below) in a variety of ways.

Figure 3:
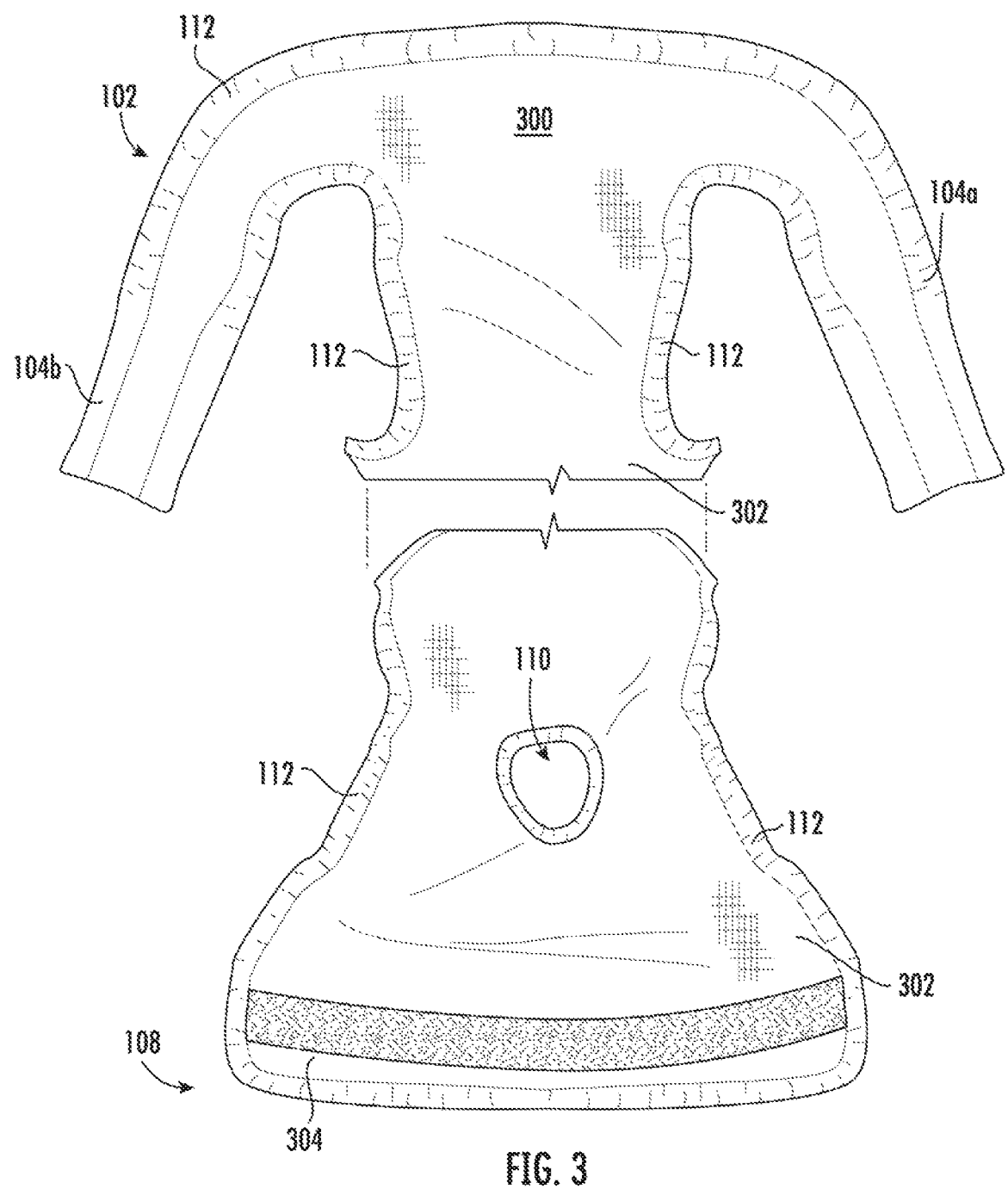
FIG. 3 illustrates a top view of the durable pet diaper showing the impervious exterior layer.

As FIG. 3 illustrates, the impervious exterior layer 300 comprises a durable fabric 302 that for most uses can be soft and lightweight generating a soft to touch characteristic. In one non-limiting embodiment, the durable fabric 302 comprises a polyester mesh fabric, but a range of nonwoven or woven fabrics can be used as long as they are strong, durable, washable, reusable and, in some embodiments, prohibit wicking. Those skilled in the art will recognize that caressing a pet 114 is a favorite activity for pet 114 owners. Thus, the soft fabric 302 of the impervious exterior layer 300 allows the pet owner to caress the pet 114 and manipulate the diaper 100 in a comfortable manner.

Figure 6:
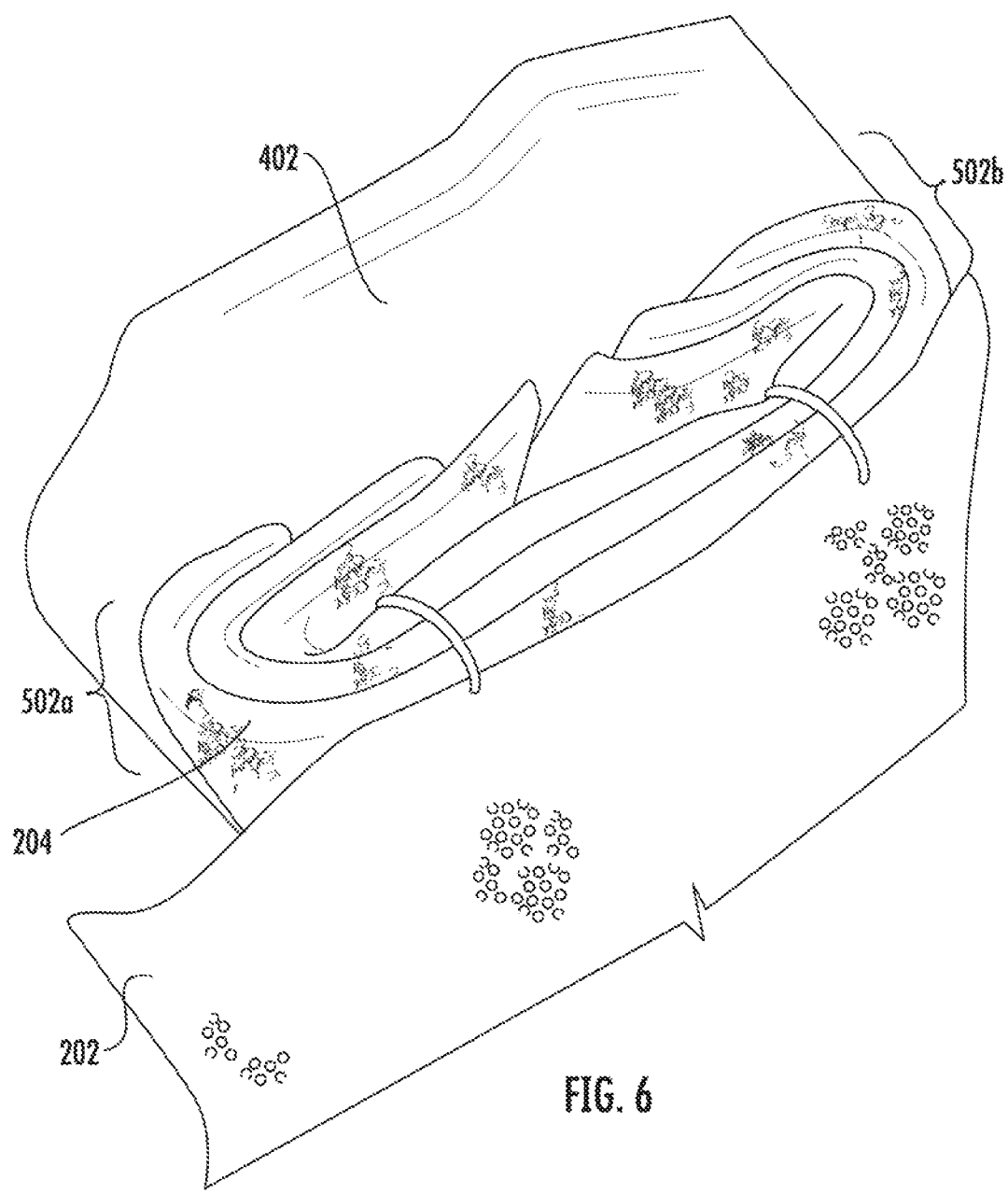
FIG. 6 illustrates the diaper cut in half showing a folded absorbent pad and adjacent fabric layers.

Looking ahead to FIG. 6, the laminate 402 (or impervious barrier film/fabric of choice) may be heat bonded to the durable fabric 302. Though in other embodiments, other means for attaching the laminate 402 to the soft lightweight durable fabric 302 may be used, including an adhesive, stitches, and fasteners. The film may also be sprayed or extruded onto the fabric. This unique integration of laminate 402 and soft lightweight durable fabric 302 optimizes the properties of each material to enable both the properties of rigidity, and a soft feel to the exterior layer 300 of the diaper 100. In some embodiments, the impervious barrier film or laminate 402 and durable fabric 302 have low wicking or non-wicking properties which increases containment of fluid to the diaper interior. Furthermore, the barrier film 402 and durable fabric 302 may contain stretch enhancing components, such as elastomers, spandex and the like.

In these embodiments, the impervious barrier film/fabric comprises the inside face of the exterior layer 300 to prevent urine from seeping through to the outside. On the other hand, the durable fabric 302 comprises the outside face of the exterior layer 300 to protect the impervious material from wear and tear during washings and to give the diaper 100 a soft to the touch exterior surface.

In one embodiment, durable fabric 300 and/or interior layer 202 can be comprised of a polyolefin based polymer, for example polypropylene, polyethylene or a blend thereof. Moreover, other natural and synthetic fibers may be used (or blends thereof alone or with other constituents) such as polyester, polyethylene, rayon, cotton, and/or polypropylene.

Figure 4:
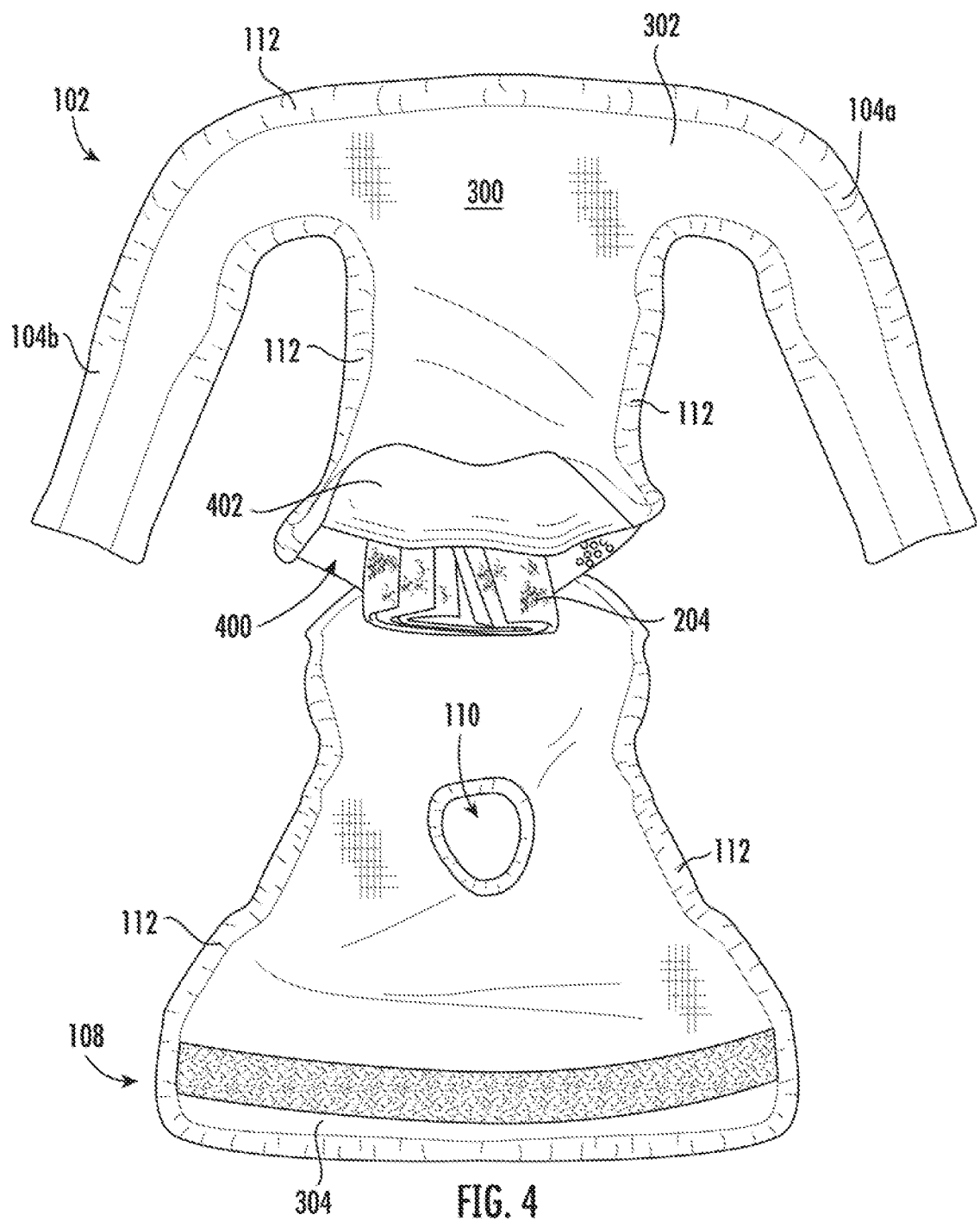
FIG. 4 illustrates a top view of the impervious layer cut open to show the impervious barrier film and the absorbent pad.

As illustrated in FIG. 4, an absorbent pad 204 is encapsulated between the exterior layer 300 and the interior layer 202. Specifically, the absorbent pad 204 may be disposed in the pocket 400 that forms between the exterior layer 300 and the interior layer 202 of the diaper 100. The absorbent pad 204 is defined by a pair of long sides 500. In one non-limiting embodiment, the long sides 500 of the absorbent pad 204 are stitched directly to the exterior and/or interior layer 202. Stitching the absorbent pad 204 into either the exterior or interior layers versus the outer rim, in some embodiments, may be preferable in order to lessen the rigidity and stiffness of the outer rim, while also retaining full elasticity or stretchability generated by elastic, spandex or the like should such be utilized in the outer rim.

Figure 5:
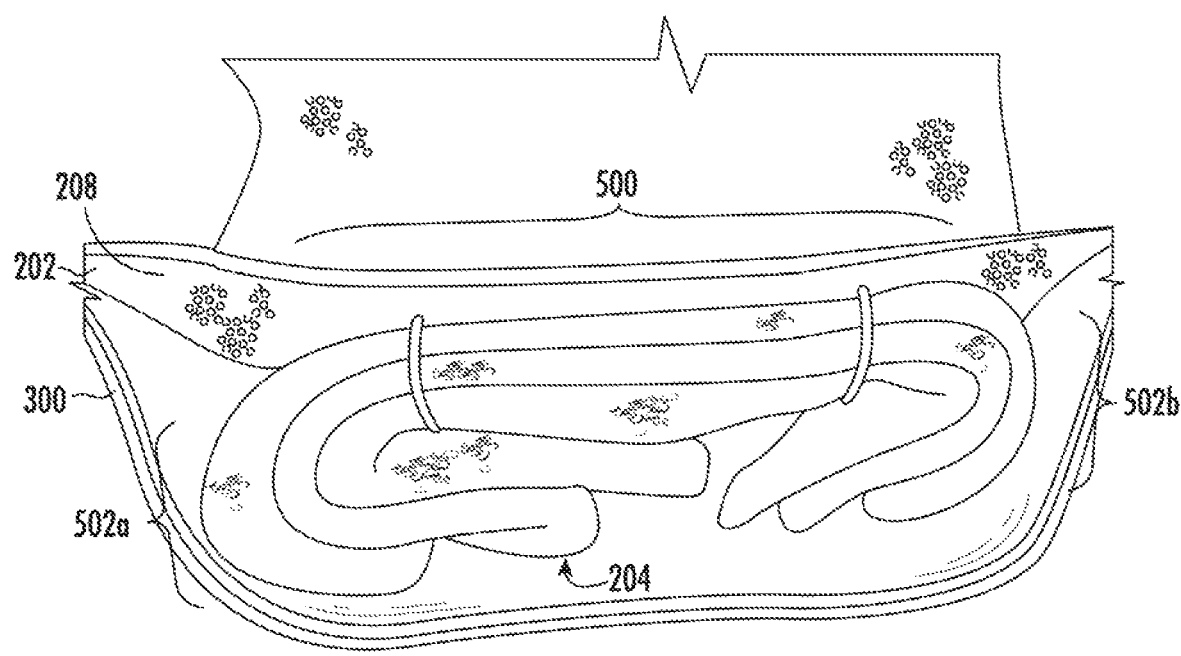
FIG. 5 illustrates the diaper cut in half showing a folded multi-plied absorbent pad and adjacent fabric layers.

In some embodiments, the absorbent pad 204 may be multi-plied (FIG. 5). The use of multiple plies of material enhances the absorbency of the pad 204. Further, the durability and reusability of the absorbent pad 204 is increased through use of multiple plies. In one non-limiting embodiment, the absorbent pad 204 is fabricated various absorbent materials, including, without limitation, a polyolefin polymer fiber, a polyester fiber, a cotton fiber, a rayon fiber, and a binder fiber. The absorbent pad 204 fibers may blended through mechanical entanglement. In one example, heat from the mechanical entanglement sets the bond of the polyolefin polymer fiber.

Further, each ply of the absorbent pad 204 may be fabricated from a different fiber/material composition. This blended configuration creates great flexibility for the absorption capacity of the pad 204. In some embodiments, the absorbent pad 204 has integrated within, fibers consisting of at least one of the following: an antimicrobial agent, a deodorant, and antifungal agent. These agents work to reduce odors from pet waste, protect the pet's anal region and anatomical features from irritation and disease, and improve sanitation.

This process increases the integrity of the ply and enhances the durability of the pad 204 dramatically. Additionally, in one embodiment, the fiber blend may Include a binder fiber, such as a low melt polyethylene, to further enhance durability of the ply. In one embodiment, absorbent pad 204 can have three identical plies with the same fiber blend constituents. In another embodiment, the pad 204 can have less than or more than three plies. In another embodiment, the pad 204 can have multiple plies each composed of different fiber blends.

Figure 7A:
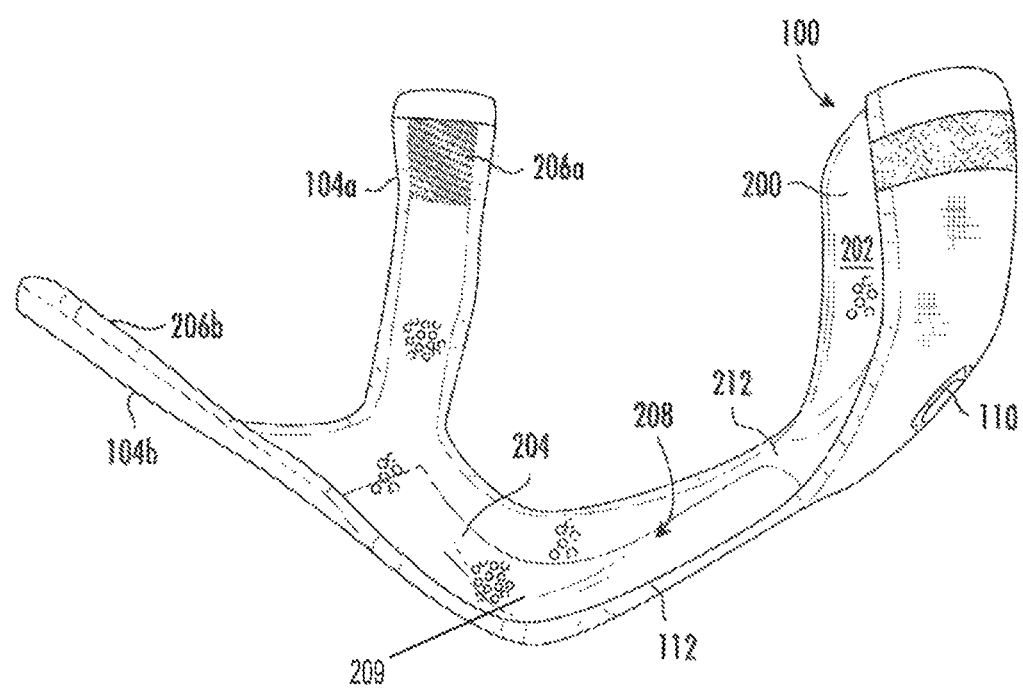
FIG. 7A illustrates a side view of a diaper to illustrate the cupping effect generated by its construction.
Figure 7B:
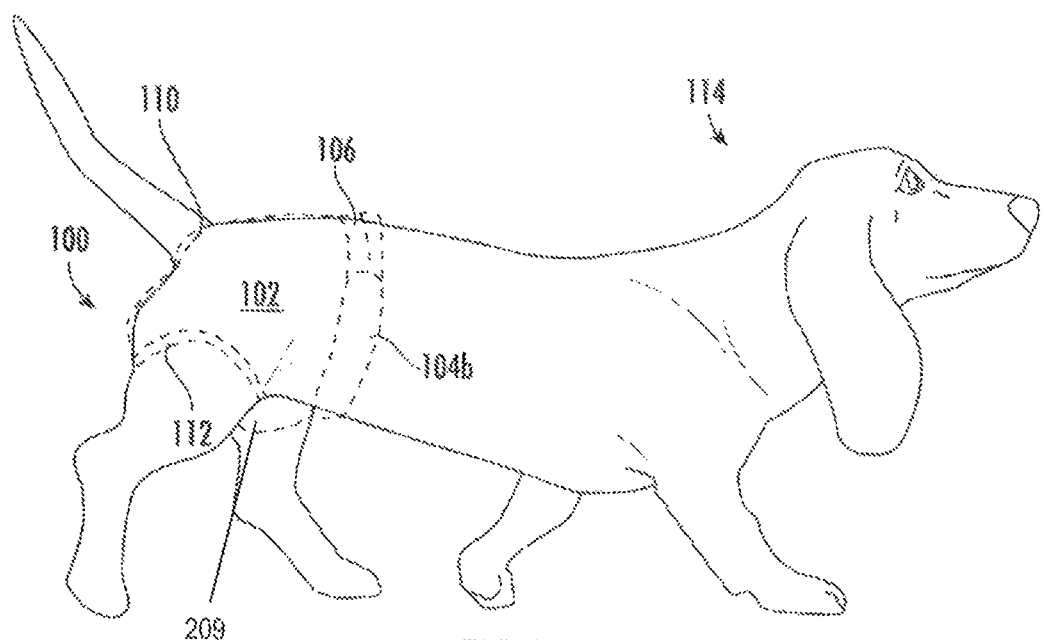
FIG. 7B illustrates a side view of a diaper secured to a pet to demonstrate its commodious fit and the cupping effect in the crotch area of the animal.

As FIG. 6 illustrates, the absorbent pad 204 is folded into at least a first fold 502a and a second fold 502b along the long sides 500. Though in other embodiments, the absorbent pad 204 can be folded in a greater amount of folds. Those skilled in the art will recognize that both the material composition, and the thickness of an absorbent pad 204 from such folding means are determinate of the absorbency rate. Thus, the absorbent pad 204 folds multiple times, not only to optimize absorbency, but also to form a small profile between inner and outer layers of the diaper 100. Specifically, the folds 502a-b work to decrease the width and space profile of the absorbent pad 204. Furthermore, folding the pad increases pad thickness and rigidity producing, along with other factors, a cupping effect thereby reducing contact between a wet pad and the animal's skin. This helps to keep the animal dry and comfortable. In some embodiments, the cupping or pocketing effect may be accomplished using other techniques that increase the thickness and rigidity of the pad during manufacturing as an alternative to folding, Looking back at FIG. 4, the absorbent pad 204 is centrally located relative to the outer rim 112 from each side. This central location positions the absorbent pad 204 distally from the outer rim 112; thereby creating a gap 208 between the long sides 500 of the absorbent pad 204, and the outer rim 112 that joins the inner and outer layers of the diaper 100. The gap 208 between the pad 204 and the outer rim 112 is sized and dimensioned to create additional space for the pet 114 and naturally forms a cup-like shape 209 which enhances comfort in the crotch area as shown in FIGS. 7A-B. This allows the pet 114 to walk, run, stretch, and scratch with the hind legs in an unencumbered manner. Thus, the folded configuration and the central position of the absorbent pad 204 create a more commodious fit on the pet's body.

Furthermore, the smaller, more discrete profile of the absorbent pad 204, as well as the stitching techniques used to attach the pad 204 to the exterior or interior layers 300, 202, and the stitching techniques used to attach the exterior and interior layers 300, 202 together, produces a cup or bowl effect generating more room inside the diaper 100 and more freedom of motion and comfort for the pet 114.

Looking back at FIG. 1, the diaper 100 is defined by a front portion 102 that substantially covers the pet's body from the crotch to the rib cage. The front portion 102 comprises a foldable front edge 106 adapted to fold outwardly and inwardly. The capacity of the front edge 106 to fold inwardly or outwardly enables the surface area of the pet's body, and specifically from the pet's crotch to the rib cage, to be adjustably increased or decreased. This is accomplished by folding the front edge 106 inwardly to decrease the surface area of the pet 114 that is covered, and folding outwardly to increase the covered surface area.

Looking again at FIG. 1, the diaper 100 comprises a back portion 108 that is a continuation of the front portion 102.

The back portion 108 is configured to substantially cover the pet's body from the rectum to the back region. In one embodiment, the back portion 108 is defined by a tail hole 110, which aligns with the tail, such that the tail can be threaded through the tail hole 110. In some embodiments, the tail hole 110 may be elasticized to allow for greater comfort to the region around the tail, including the anal region. The elasticized tail hole 110 also allows a hand to fit into the diaper 100, beneath the interior layer 202, to thread the tail through the tail hole 110, and to feel the pet 114.

Turning again to FIG. 2, the diaper 100 provides one or more resilient flaps 104a, 104b that extend from the front portion 102. The resilient flaps 104a-b extend from the front portion 102 of the diaper 100, extending towards the back portion 108 to secure the front portion 102 and the back portion 108 of the diaper 100 to the pet 114. The flaps 104a-b adjustably extend and retract longitudinally across the pet's midsection and ribcage when securing the front and back portions 102, 108 together.

As illustrated in FIG. 3, the flaps 104a, 104b may include one or more first securing elements 206a, 206b that fasten to second securing element 304 on a back portion 108 of the diaper 100, as described below. The first securing elements 206a-b may comprise hook and loop fasteners. Though in other embodiments, the first securing elements 206a-b may include, without limitation, an adhesive, a snap button, a pin, and a tying string.

In some embodiments, the back portion 108 may include at least one second securing element 304 that is adapted to detachably mate with the first securing elements 206a, 206b on the flaps 104a, 104b that extend from the front portion 102. The first and second securing elements 206a-b, 304 are configured to detachably mate with each other, so that the diaper 100 can be easily removed from the pet 114.

In one embodiment, the second securing element 304 extends across the outer rim 112 of the back portion 108. Similar to the first securing elements 206a-b, the second securing element 304 may include hook and loop fasteners. Though in other embodiments, the second securing element 304 may include, without limitation, an adhesive, a snap button, a pin, and a tying string.

In one non-limiting embodiment, the one or more flaps 104a, 104b comprise two elongated flaps having rounded edges. Though a greater number of flaps may be used, depending on the size and movement activity of the pet 114. The flaps 104a-b are sufficiently resilient to extend and retract longitudinally across the pet's midsection and ribcage, so as to enable unrestricted movement and a commodious fit for the pet 114. Thus, the resilient flaps 104a-b secure the diaper 100 to the pet 114 in an adjustable manner that creates a commodious fit on the pet's body, enabling the pet 114 to walk, run, stretch, and scratch comfortably while wearing the diaper 100.

In another embodiment intended principally for male animals, the pet diaper may be a substantially rectangular wrap for placement and attachment around, the animal's midsection, covering portions or all of the crotch area, penis and torso. The wrap durable diaper design does not accommodate the legs or tail (e.g., it does not contain holes for the legs or tail).

A method for diapering a pet 114 with a durable pet diaper 100 is also disclosed. The method may include an initial step of providing a pet diaper 100, the pet diaper 100 comprising a front portion 102 and a back portion 108 joined at an outer rim 112, the back portion 108 being defined by an elasticized tail hole 110, and one or more flaps 104a-b extending from the front portion 102 and adapted to detachably mate with the back portion 108 for securing the front and back portion 102, 108 to the pet 114. In some embodiments, the front portion 102 being defined by a foldable front edge 106.

The method may further comprise a step of threading the pet's tail through the elasticized tail hole 110. The elasticization of the tail hole 110 facilitates threading the tail through. Another step relates to positioning the back portion 108 such that the outer rim 112 rests on the pet's back at or near the lower rib cage. The back portion 108 can be manipulated against the pet's skin or fur to achieve the desired position on the pet 114. A user may then position the front portion 102 such that the outer rim 112 rests on the pet's crotch, rib cage or torso. The front portion 102 can be manipulated against the pet's skin or fur to achieve the desired position on the pet 114.

In some embodiments, the foldable from edge 106 can be adjustably, folded inwardly or outwardly to decrease and increase the surface area covered from the pet's crotch to the rib cage. This may be useful for creating greater comfort to the pet 114. For example, increasing surface area coverage on the pet's skin or fur in the cold, and decreasing surface area coverage in the heat. In some embodiments, a user may pull the flaps 104a-b around the pet's midsection, across the sides, and over the back of the pet 114. The flaps 104a-b are sufficiently resilient to extend and retract longitudinally across the pet's midsection and ribcage, so as to enable unrestricted movement and a commodious fit for the pet 114.

In some embodiments, a first securing element on the flaps 104a-b can be engaged with a second securing element 304 on the back portion 108 of the diaper 100. This forms a snug fit for the front and back portions 102, 108 on the pet 114. A final includes adjustably extending and retracting the flaps 104a-b longitudinally across the pet's midsection to provide a commodious fit for the pet 114. The flaps 104a-b can be stretched, pulled up, and pulled down across the pet's midsection and ribcage to achieve the desired fit on the pet 114.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by, the appended claims and their legal equivalence.

What is claim is:
1. A durable pet diaper, the diaper comprising:
an unfolded outer fabric diaper shaped cover comprising a substantially impervious exterior layer comprising a polyester mesh fabric with a polyvinyl chloride laminate configured across the surface of the exterior layer to enhance diaper structural integrity and durability, a substantially pervious and breathable interior layer, and an outer perimeter defining the diaper shape, the layers being joined together at a junction positioned about said outer perimeter forming a pocket space between the interior and exterior layers, wherein said pocket space terminates at the junction and is positioned beneath the crotch when the diaper is worn by the pet;

an elongated absorbent pad comprising a top end, a bottom end, a first lateral side and a second lateral side and centrally positioned within said pocket space, wherein said top end, bottom end, first lateral side, and second lateral side are distal from said junction leaving vacant pocket space between said top end, bottom end, first lateral side, second lateral side and said junction;

a front portion substantially covering from the pet's crotch to the abdominal midsection comprising one or more resilient flaps extending from the front portion of the diaper, the flaps comprising one or more first securing elements; and a back portion comprising at least one second securing element adapted to detachably mate with the first securing elements, wherein the flaps secure the front portion and the back portion of the diaper to the pet and adjustably extend and retract longitudinally across the pet's midsection when the front and back portions are secured to the pet.

2. The diaper of claim 1, wherein the polyester mesh fabric comprises a soft lightweight durable fabric.

3. The diaper of claim 1, further comprising a comfort cup within the general area of the absorbent pad and pocket.

4. The diaper of claim 3, wherein the absorbent pad is a nonwoven comprising polyolefin polymer fiber fabric constitution.

5. The diaper of claim 4, wherein the fabric constitution comprises at least one of the following: a polyolefin polymer fiber, a polyester fiber, a cotton fiber, a rayon fiber, and a binder fiber.

6. The diaper of claim 5, wherein the absorbent pad is attached to the interior layer.

7. The diaper of claim 5, wherein the absorbent pad fibers are blended through mechanical entanglement, wherein heat sets the bond of the polyolefin polymer fiber.

8. The diaper of claim 7, wherein each ply of the absorbent pad has a different configuration of fibers.

9. The diaper of claim 8, wherein the fibers include at least one of the following: an antimicrobial agent, a deodorant, and an antifungal agent.

10. The diaper of claim 1, wherein the absorbent pad is multi-plied.

11. The diaper of claim 1, further comprising an aperture adapted to receive a tail therethrough, wherein said aperture and outer rim comprise elastic for stretchability.

12. The durable pet diaper of claim 1, wherein the back portion comprises a tail hole and substantially covers from the pet's rectum to the back.

13. The durable pet diaper of claim 1, wherein the diaper is in the form of a rectangular wrap for crotch coverage and urine containment in pets.

14. The durable pet diaper of claim 1, wherein said outer rim comprises elastic and a binding fabric enveloping said elastic which improves fit and prevents solid and liquid waste from escaping.

15. A method for reusable pet waste containment, the method comprising:

providing a durable pet diaper, the pet diaper comprising an outer fabric covering comprising a substantially impervious exterior layer comprising a polyester mesh fabric with a polyvinyl chloride laminate configured across the surface of the exterior layer to enhance diaper structural integrity and durability, a substantially pervious and breathable interior layer, a front portion and a back portion joined at an outer rim, the back portion being defined by an elasticized tail hole, and one or more flaps extending from the front portion and adapted to detachably mate with the back portion for securing the front and back portions to a pet;

threading the pet's tail through the elasticized tail hole;

positioning the back portion such that the outer rim rests on the pet's back at or near the lower rib cage;

positioning the front portion such that the outer rim rests on the pet's crotch rib cage;

pulling the flaps around the pet's midsection, across the sides, and over the back of the pet;

engaging a first securing element on the flaps with a second securing element on the back portion;

adjustably extending and retracting the flaps longitudinally across the pet's midsection to provide a commodious fit for the pet; and removing the pet diaper from the pet when desired and laundering the pet diaper for reuse.

16. The method of claim 15 wherein the front portion of the pet diaper comprises a foldable front edge and the additional step of adjustably folding the foldable front edge inwardly or outwardly to adjustably decrease and increase the surface area covered from the pet's crotch to the rib cage.

17. A method for reusable pet waste containment, the method comprising:

providing a durable pet diaper, the pet diaper comprising an outer fabric cover comprising a substantially impervious exterior layer comprising a polyester mesh fabric with a polyvinyl chloride laminate configured across the surface of the exterior layer to enhance diaper structural integrity and durability, and a substantially pervious and breathable interior layer, the layers being joined together along an outer rim of the diaper and forming a pocket therebetween;

an absorbent pad comprising one or more sides and contained within the pocket formed between the exterior layer and the interior layers, the absorbent pad having a profile with dimensions smaller than the space formed between interior and exterior layers causing a spatial gap to form between the sides of the absorbent pad and the outer rim of the diaper;

a front face comprising a first end comprising one or more first securing elements; and a back face comprising a first end comprising one or more second securing elements adapted to detachably mate with the first securing elements, wrapping the pet diaper around the pet's midsection whereby the absorbent pad and pocket are in substantial alignment with the pet's crotch area and whereby the diaper substantially covers from the pet's crotch to abdominal midsection;

positioning the ends of the front and back portions such that the first and second securing elements are proximate to one another;

applying tension to the ends of the front and back portions for snug fit around the pet's midsection;

engaging first securing element with second securing element to secure the diaper to the pet; and removing the pet diaper from the pet when desired and laundering the pet diaper for reuse.

\* \* \* \* \*